United States Patent
Jackson et al.

[11] Patent Number: 5,934,140
[45] Date of Patent: Aug. 10, 1999

[54] PAPER PROPERTY SENSING SYSTEM

[75] Inventors: Warren B. Jackson, San Francisco; David K. Biegelsen, Portola Valley; Andrew A. Berlin, Palo Alto; Robert A. Sprague, Saratoga; Todd A. Cass, San Francisco, all of Calif.

[73] Assignee: Xerox Corporation, Stamford, Conn.

[21] Appl. No.: 08/667,040

[22] Filed: Jun. 19, 1996

[51] Int. Cl.⁶ .............................. G01N 21/86; G01B 3/00
[52] U.S. Cl. ................. 73/159; 250/559.27; 271/265.04; 399/389; 33/501.04
[58] Field of Search ................ 250/559.27, 559.29, 250/559.31; 355/133, 408; 356/381; 73/159; 33/501.02, 501.03, 501.04, 807, 783; 399/45, 389; 271/265.04, 265.03, 265.02, 265.01, 258.04, 258.01, 263, 262

[56] References Cited

U.S. PATENT DOCUMENTS

| | | | |
|---|---|---|---|
| 2,806,373 | 9/1957 | Bendtsen | 73/159 |
| 3,565,531 | 2/1971 | Kane et al. | 250/559.27 X |
| 3,892,043 | 7/1975 | Bonikowski | 33/501.04 |
| 4,141,253 | 2/1979 | Whitehead, Jr. | 73/727 |
| 4,151,502 | 4/1979 | Kurihara et al. | 338/2 |
| 4,224,513 | 9/1980 | Casey et al. | 250/216 |
| 4,277,177 | 7/1981 | Larsen et al. | 356/431 |
| 4,348,102 | 9/1982 | Sessink | 355/14 |
| 4,419,023 | 12/1983 | Hager, Jr. | 374/179 |
| 4,493,548 | 1/1985 | Ateya | 355/3 FU |
| 4,528,507 | 7/1985 | Domin et al. | 324/229 |
| 4,610,530 | 9/1986 | Lehmbeck et al. | 355/14 TR |
| 4,641,949 | 2/1987 | Wallace et al. | 355/3 SH |
| 4,937,460 | 6/1990 | Duncan et al. | 250/559.27 |
| 4,941,269 | 7/1990 | Mori et al. | 33/501.04 X |
| 4,966,455 | 10/1990 | Avni et al. | 356/73 |
| 5,109,236 | 4/1992 | Watanabe et al. | 346/76 PH |
| 5,174,562 | 12/1992 | Mizunaga et al. | 271/261 |
| 5,204,537 | 4/1993 | Bennet et al. | 250/559.27 X |
| 5,276,327 | 1/1994 | Bossen et al. | 250/339 |
| 5,389,795 | 2/1995 | Rye | 250/572 |
| 5,486,063 | 1/1996 | Fox et al. | 250/559.27 X |
| 5,490,089 | 2/1996 | Smith et al. | 364/514 R |
| 5,511,428 | 4/1996 | Goldberg et al. | 73/777 |
| 5,727,692 | 3/1998 | Large et al. | 209/603 |

FOREIGN PATENT DOCUMENTS

| | | |
|---|---|---|
| 0 650 100 A2 | 4/1995 | European Pat. Off. . |
| 43 37 094 A 1 | 5/1995 | Germany . |
| 44 11 957 A 1 | 10/1995 | Germany . |
| 59-166841 | 9/1984 | Japan . |
| 3282206 | 12/1991 | Japan ................ 356/381 |
| 1696988-A1 | 12/1991 | U.S.S.R. . |
| WO 92/11505 | 7/1992 | WIPO . |

OTHER PUBLICATIONS

Bryzek, J. et al., Micromachines on the March. IEEE Spectrum, May 1994, pp. 20–31.

Konishi, S. et al., A Conveyance System Using Air Flow Based on the Concept of Distributed Micro Motion Systems. Journal of Microelectromechanical Systems, vol. 3, No. 2, Jun. 1994, pp. 54–58.

(List continued on next page.)

*Primary Examiner*—George Dombroske
*Assistant Examiner*—Willie Morris Worth

[57] ABSTRACT

A sensor system for measuring physical properties of a sheet. In one embodiment, the sensor system measures paper curl and thickness using two sensors, each of which includes a member, a base, and measurement circuit. The two members are positioned in opposition to each other and both contact the sheet as it passes between them. Each member is coupled to a base, which includes a measurement circuit. Each measurement circuit measures the displacement of its associated member. In another embodiment, the sensor system measures stiffness and curl using two pairs of opposed sensors. In yet another embodiment, the sensor system measures thermal diffusivity of a sheet of paper using three sensors, one of which includes a heater for heating the sheet of paper and the other two sensors include thermocouples in contact with the sheet of paper for sensing the heat of the paper.

12 Claims, 6 Drawing Sheets

OTHER PUBLICATIONS

Konishi, S. et al., System Design for Cooperative Control of Arrayed Microactuators. Proceedings of the IEEE Micro Electro Mechanical Systems 1995, IEEE, Piscataway, NJ, USA 95CH35754, pp. 322–327.

Paivanas, J.A. et al., Air Film System for Handling Semiconductor Wafers. IBM J. Res. Develop., vol. 23, No. 4, Jul. 1979, pp. 361–375.

European Search Report for EPO counterpart Application No. 97304181.7. Nov. 3, 1997.

PAPER PROPERTY SENSING SYSTEM

FIELD OF THE INVENTION

The present invention relates to sensor systems for paper handling devices. The disclosed sensor systems are suitable for determining paper properties such as paper thickness, curl, mass, and stiffness.

BACKGROUND OF THE INVENTION

The quality of text or images written to or read from a markable medium such as paper by devices such as laser printers, xerographic printers, scanners, or ink jet printers is highly dependent on physical characteristics of the markable medium. The thickness, curl, mass, and stiffness of the medium being marked all affect the speed and accuracy with which a printer can transport a sheet of the markable medium, as well as affecting the accuracy with which text or images can be transferred to the markable medium. Generally, printers and copiers work well only with a limited range of paper and media types, with a sheet transport mechanism and an image transfer mechanism optimized for that range. In extreme cases, reasonable print quality is only possible with specially developed paper supplied by the manufacturer and maintained in pristine condition, unbent and at certain humidity levels to limit curling. Paper that is too thick, too thin, or even slightly curled may increase the risk of jamming or blocking the sheet transport mechanism.

Using various paper type settings, printers, copiers, and scanners might prevent errors in paper transport, and increase image quality without necessarily requiring specific manufacturer supplied papers. For example, a user could manually select a "thick paper" setting if thicker papers or thin cardboard stock is to be fed through the sheet transport mechanism. Spacing of pinch rollers and speed of transport would then be automatically adjusted to compensate for the increased paper thickness. Unfortunately, this solution requires extra effort from a user to identify the correct grade or type of paper being supplied to the printer. Further, this system is somewhat unwieldy if multiple paper types are intermixed, since the "thick paper" setting must be regularly enabled and disabled by the user as various paper types are fed through the sheet transport mechanism.

Thus, a need exists for an inexpensive paper handling system that automatically detects paper properties, and automatically adjusts settings of a sheet transport mechanism to optimize sheet handling speed, spacing, or other sheet transport characteristics based on the detected paper properties. Such a system would require minimal input from a user, and would automatically attempt to optimize its sheet handling characteristics to support use of a wide range of papers and paper conditions. Such a sheet handling system would allow for greater use of recyclable papers of differing quality and consistency, and could limit paper wastage by permitting use of lower quality or even slightly damaged papers, while still providing transport results comparable to those of pristine, newly manufactured papers.

Additionally, a need exists for a sheet handling system that provides information concerning paper properties to allow for optimizing adjustments in an image transfer mechanism. If paper properties such as heat capacity, thermal conductivity, dielectric constants, or resistance are known prior to image transfer, the image transfer mechanism can be suitably optimized to ensure the best possible text or image transfer. For example, if the thermal conductivity of the paper is known, the temperature of toner fusing module in a xerographic printer can be adjusted to optimally fix toner particles to paper without wasting energy through unneeded thermal heating of the paper, which may damage the paper.

SUMMARY OF THE INVENTION

An object of the present invention is to enable automatic adjustment of sheet handling in response to physical properties of a sheet of a markable medium, like paper.

Another object of the present invention is to enable optimization of sheet transport mechanisms to permit use of a wide range of markable mediums, like paper and transparencies.

A still further object of the present invention is to reduce paper wastage by reducing jams in sheet transport mechanisms.

A sensor system satisfying these and other objects will be described. In one embodiment, the sensor system measures sheet curl and thickness using two sensors, each of which includes a member, a base, and a measurement circuit. The two members are positioned in opposition to each other, both contacting a sheet of a markable medium as it passes between them. Each member is coupled to a base, which includes a measurement circuit. Each measurement circuit measures the displacement between its associated member and base. In another embodiment, the sensor system measures sheet stiffness and curl using two spaced apart pairs of opposed sensors. In yet another embodiment, the sensor system measures the thermal diffusivity of a sheet using three sensors, one of which includes a heater for heating the sheet and the other two sensors include thermocouples in contact with the sheet for sensing its heat.

Other objects, features, and advantages of the present invention will be apparent from the accompanying drawings and detailed description that follows.

BRIEF DESCRIPTION OF THE DRAWINGS

The present invention is illustrated by way of example and not by way of limitation in the figures of the accompanying drawings. In the accompanying drawings similar references indicate similar elements.

DETAILED DESCRIPTION OF THE PREFERRED EMBODIMENTS

Figure 1:
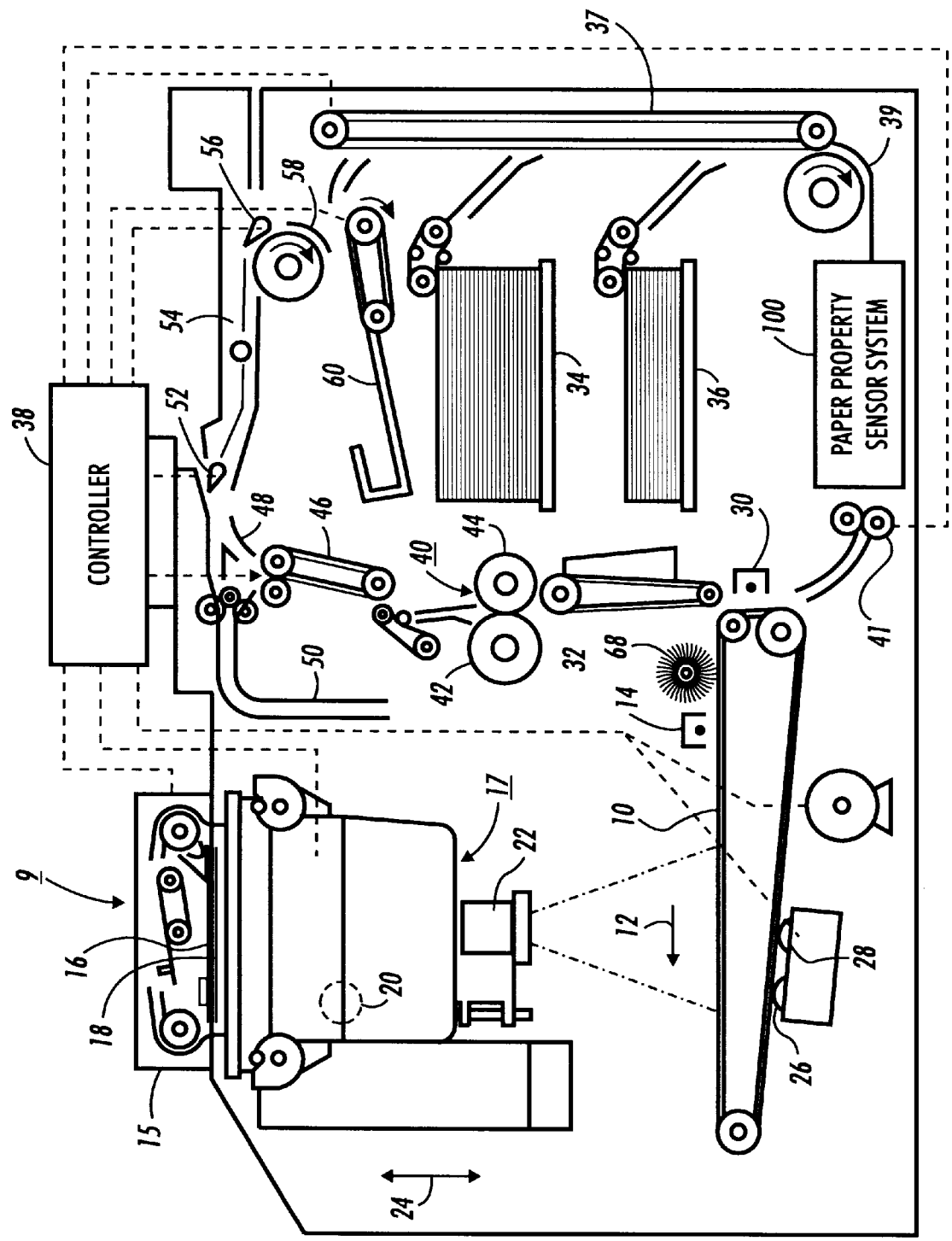
FIG. 1 illustrates a reproductive machine incorporating the paper property sensor system of the present invention.

FIG. 1 illustrates a reproductive machine 9 incorporating paper property sensor system 100 of the present invention. Paper property sensor system 100 enables reproductive machine 9 to alter its handling of sheets of a markable medium in response to properties of the markable medium currently within machine 9. Paper property sensor system 100 may also be used in conjunction with any machine that uses materials such as transparencies, metal, plastic, and silicon wafers. Briefly described, each embodiment of paper property sensor system 100 includes one or more paper property sensors, each of which includes a member coupled to a base and a measurement unit. Various properties of the medium being transported can be determined by measuring the displacement of the member relative to the base. Paper property sensor system 100 will be described in detail with respect to FIGS. 2–7.

A. The Reproductive Machine

Prior to a more detailed discussion of the paper property sensor system 100 of the present invention, consider reproductive device 9, illustrated in FIG. 1. Reproductive machine 9 includes a belt 10 having a photoconductive surface. Belt 10 moves in the direction of arrow 12 to advance successive portions of the photoconductive surface through various processing stations, starting with a charging station. The charging station includes corona generating device 14, which charges the photoconductive surface to a relatively high, substantially uniform, potential.

From the charging station, the photoconductive surface is advanced through an imaging station. At the imaging station, document handling unit 15 positions original document 16 face down over exposure system 17. Exposure system 17 includes lamp 20, which illuminates document 16 on transparent platen 18. The light rays reflected from document 16 are transmitted through lens 22, focusing the light onto the charged portion of belt 10 to selectively dissipate the charge. This records an electrostatic latent image of document 16 on photoconductive surface of belt 10.

Platen 18 is mounted movably and moves in the directions of arrows 24 to adjust the magnification of the original document being reproduced. Lens 22 moves synchronously with platen 18 to focus the light image of document 16 onto the charged portion of belt 10.

A document handling unit sequentially feeds documents from a holding tray, in seriatim, to platen 18. The document handling unit recirculates paper back to the stack supported on the tray. Thereafter, belt 10 advances the electrostatic latent image to a development station.

At the development station a pair of magnetic brush developer rollers 26 and 28 move a developer into contact with the electrostatic latent image on belt 10. The latent image attracts toner particles from the developer to form a toner powder image on belt 10.

After development of the electrostatic latent image, belt 10 advances to the transfer station. At the transfer station a copy sheet is moved into contact with the toner powder image. The transfer station includes generating device 30, which sprays ions onto the backside of the copy sheet. This attracts the toner powder image from the photoconductive surface of belt 10 to the copy sheet.

The copy sheet is fed from either tray 34 or 36 to the transfer station. After transfer, conveyor 32 advances the sheet to fusing station 40. Fusing station 40 includes a fuser assembly for permanently affixing the transferred powder image to the copy sheet. Preferably, fuser assembly 40 includes a heated fuser roller 42 and a backup roller 44.

Paper property sensor system 100 is disposed between copy paper trays 34 and 36 and conveyor 32 at any convenient location, or locations, within the copy paper transport path. Preferably, paper property sensor system 100 is located close to copy paper trays 34 and 36. Information provided by paper property sensor system 100 allows controller 38 to prevent jams by adjusting the speed of conveyors 32, 37 and 46, and the spacing between nips 39 and 41, between rollers 42 and 44, gates 48 and 52, and decision gate 52.

Controller 38 includes a processor and memory. The processor controls and coordinates the operations of reproductive machine 9 by executing instructions stored electronically in memory, including instructions for controlling paper property sensor system 100. Instructions representing the methods discussed herein may be realized in any appropriate machine language. Semiconductor logic devices that can be used to realize memory include read only memories (ROM), random access memories (RAM), dynamic random access memories (DRAM), programmable read only memories (PROM), erasable programmable read only memories (EPROM), and electrically erasable programmable read only memories (EEPROM), such as flash memories.

B. A First Paper Property Sensor System for Measuring Thickness and Curl

Figure 2A:
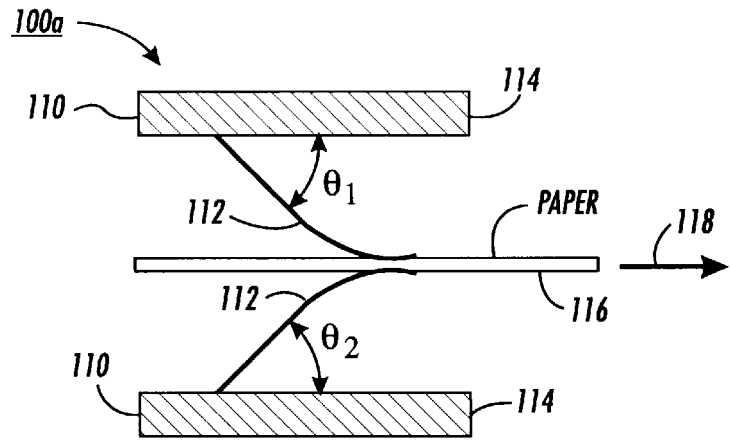
FIG. 2A illustrates an embodiment of a paper property sensor system for measuring sheet thickness and curl.

FIG. 2A illustrates a first embodiment 100a of paper property sensor system 100, which enables measurement of sheet thickness and curl. Connections between paper property sensor system 100a and controller 38 are not illustrated in FIG. 2A; nor are they illustrated in subsequent figures. Paper property sensor system 100a includes a pair of opposed paper property sensors 110. Paper property sensors 110 are used in each embodiment of paper property sensor system, consequently, the following discussion of sensors 110 applies equally to all system 110, unless otherwise stated.

Each paper property sensor 110 includes a member 112 coupled to, and extending longitudinally from base 114. Each base 114 includes a measurement circuit for measuring the angle, θ, of member 112 relative to base 114. Various properties can be measured as sheet 116 passes between members 112, contacting and deflecting members 112. Arrow 118 indicates the transport direction of sheet 116.

Preferably, paper property sensor 110 is fabricated as a microelectromechanical type (MEMs type) device using standard semiconductor batch fabrication and wafer processing. This approach allows paper property sensor 110 to be fabricated at a cost of a few pennies and results in a device with dimensions on the order millimeters. This small size is not necessary to the functionality of paper property sensor 110; however, producing larger devices with other techniques is likely to increase the cost per paper property sensor.

Member 112 can be realized as a long slender arm extending longitudinally from base 114, as shown in FIG.

Figure 2B:
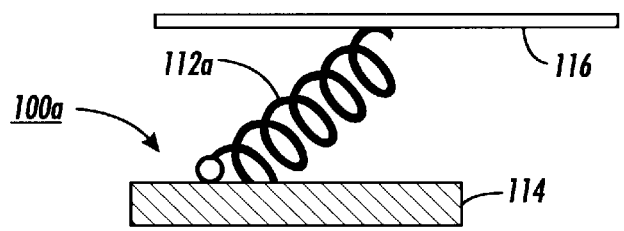
FIG. 2B illustrates an alternative embodiment of a member of a paper property sensor.
Figure 2C:
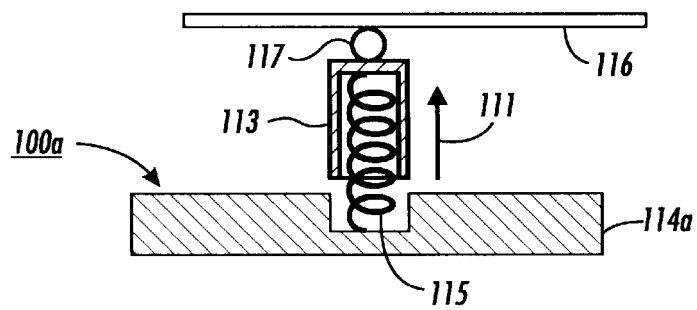
FIG. 2C illustrates another alternative embodiment of a member of a paper property sensor.

2A. Alternatively, member 112 can be realized as a spring as shown in FIG. 2B. The embodiments of member 112 of both FIGS. 2A and 2B can be fabricated using low mass materials and processes including releasing thick metal overlayers on silicon or glass using sacrificial underlayers, or bonding preformed springs for example. Alternatively, if paper property sensor 110 is not to be realized using batch semiconductor processing then member 112 can be realized in other ways. In FIG. 2C member 112 is realized as a spring-loaded plunger. Spring 115 allows plunger 113 to move up and down in the direction of arrow 111 as sheet 116 passes over roller 117. Plunger 113 is shown coupled to base 114 perpendicularly. Alternatively, plunger 113 may be coupled at a lesser angle to prevent impeding the movement of sheet 116. Plunger 113 can be replaced with a solenoid activated valve. However realized, deflection of member 112 by paper 116 changes the angle of member 112 with respect to its associated base. In subsequent drawings, member 112 is illustrated as an arm; however, the following discussion applies to all embodiments of member 112.

Figure 2D:
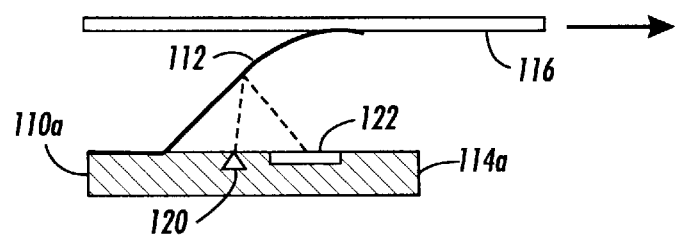
FIG. 2D illustrates a first embodiment of a paper property sensor.
Figure 2E:
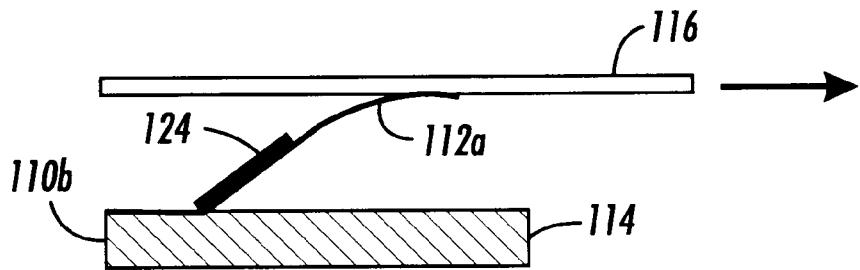
FIG. 2E illustrates a second embodiment of a paper property sensor.
Figure 2F:
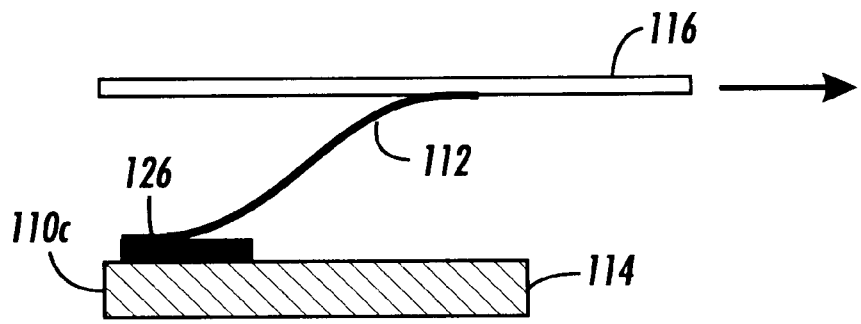
FIG. 2F illustrates a third embodiment of a paper property sensor.
Figure 2G:
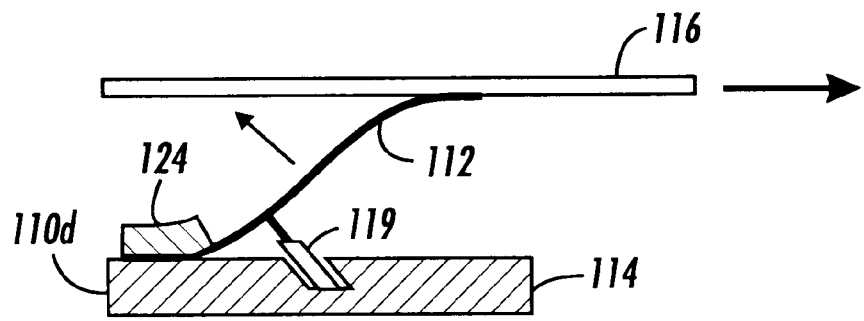
FIG. 2G illustrates a fourth embodiment of a paper property sensor.

FIG. 2D illustrates a first embodiment 110a of paper property sensor 110. Base 114a includes a measurement circuit having a light source 120, preferably a light emitting diode (LED) 120, and position detector 122. Position detector 122 detects light from LED 120 deflected by sensor arm 112. Changes in the angle between sensor arm 112 and base 114 change the location at which light hits position detector 122, thereby changing the signal output by the measurement circuit to controller 38. FIG. 2E illustrates a second embodiment 110b of paper property sensor 110. The measurement circuit includes strain gauge 124 coupled to sensor arm 112 and base 114. Strain gauge 124 may be incorporated in sensor arm 112 and base 114, attached to sensor arm 112, or may even be attached between sensor arm 112 and base 114. Changes in the angle of sensor arm 112 relative to base 114, or changes in the flexure of sensor arm 112, change the strain sensed by strain gauge 124, thereby changing the signal coupled by the measurement circuit to controller 38. Strain gauge 124 can sense strain using piezoresistivity or piezoelectricity, for example.

Paper property sensor system 100a can measure sheet thickness and curl using either paper property sensor 110a or 110b. Measurement of sheet thickness begins without sheet 116 between sensor arms 112 and determination of a differential offset displacement, $\theta_{offset}$, where $\theta_{offset} = \theta_{1offset} - \theta_{2offset}$. Afterward, with sheet 116 between sensor arms 112, the differential displacement, $\theta_{wp}$ is measured. $\theta_{wp}$ is defined as the difference between $\theta_{1wp} - \theta_{2wp}$. Using $\theta_{wp}$ and $\theta_{offset}$ the thickness of sheet 116 can be determined by controller 38. Measurement of curl begins by measuring the differential displacement at a first time, $\theta_{\tau1}$, with sheet 116 between paper property sensors 110. At a second time, when sheet 116 has moved, but is still between paper property sensors 110, the differential displacement, $\theta_{\tau2}$, is measured. Controller 38 uses the difference between $\theta_{\tau2}$ and $\theta_{\tau1}$ as an indicator of curl. The greater the difference the greater the curl.

C. A Second Paper Property Sensor System for Measuring Sheet Mass

Figure 3:
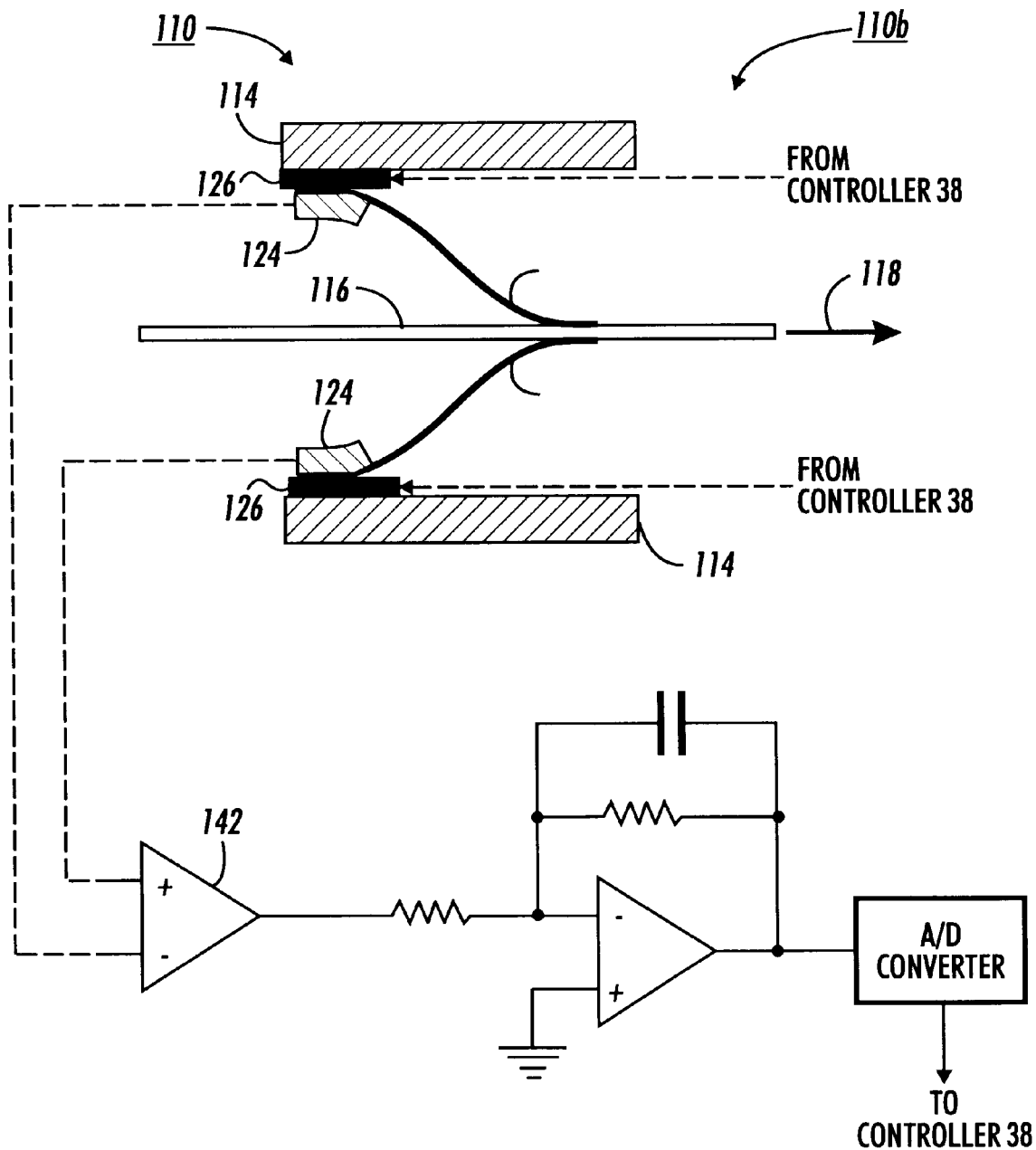
FIG. 3 illustrates an embodiment of the paper property sensor system for measuring paper mass.

FIG. 3 illustrates a second embodiment 100b of paper property sensor system 100 for measuring sheet mass. System 100b includes modified paper property sensors 110 to allow control of the positioning of sensor arms 112. FIG. 3 illustrates one type of modified paper property sensor 110c, which includes vertical actuator 126 coupled between sensor arm 112 and base 114. Vertical actuator 126 may be used in conjunction with either of the measurement circuits discussed with respect to FIGS. 2D and 2E. The mechanisms that may be used to realize vertical actuator 126 include piezoelectric bimorph elements, linear piezo-elements with mechanical amplifiers, and bubble driven micro-pistons, for example. Alternatively, paper property sensor system 100b may include the paper property sensor 110 shown in FIG. 2G. In this embodiment, vertical actuator 126 is replaced with linear actuator 119 for moving arm 112.

Paper property sensor system 100b includes circuit 140 to sense the movement of sensor arms 112. Circuit 140 takes the outputs of strain gauges 124 and feeds them to opamp 142, which functions as a differential amplifier. Low pass filter 144 separates high frequency components of the difference signal output by opamp 142, thereby allowing faithful feedback tracking. The analog output from filter 144 is then converted to a digital signal by an A/D converter prior to being coupled to controller 38. Alternatively, the A/D converter may be incorporated into controller 38.

Paper mass measurement with paper property sensor system 100b begins with a signal from controller 38, applied to actuators 126, that causes application of a vertical impulsive force of fixed amplitude to sensor arms 112 without sheet 116 therebetween. The differential displacement, $\theta_{base}$, is then sensed by the measurement circuits and coupled to controller 38, providing a baseline for comparison. Afterward, with sheet 116 between sensor arms 112, a vertical impulsive force of the same magnitude is applied to sensor arms 112 and the differential displacement $\theta_{load}$, is sensed. Controller 38 can estimate the mass of paper 116 by taking the difference between $\theta_{load}$ and $\theta_{base}$.

D. A Third Paper Property Sensor System for Measuring Curl and Stiffness

Figure 4:
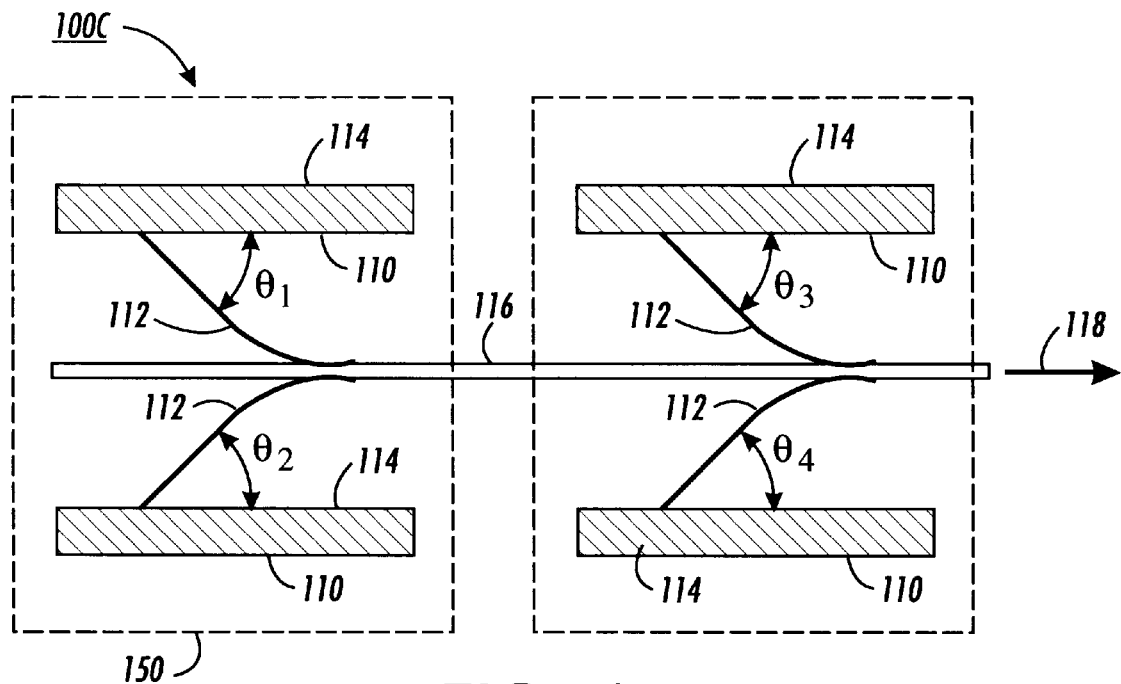
FIG. 4 illustrates an embodiment of a paper property sensor system for measuring paper stiffness and curl.

FIG. 4 illustrates an embodiment 100c of paper property sensor system 100, which can be used to measure both sheet curl and stiffness. Paper property sensor system 100c includes two pairs 150 and 152 of opposed paper property sensors 110. Vertical or linear actuators may be added to paper property sensors 110 to ensure contact between members 112 and sheet 116. Determining sheet curl using system 100c involves measuring at the same time the differential displacement sensed by both pairs of opposed paper property sensors 150 and 152 while sheet 116 is between them. The difference between the two differential displacements is indicative of curl and can be used by controller 38 to modify the operation of reproductive machine 9. Sheet stiffness can also be measured using paper property sensor system 100b provided that the first pair of paper property sensors 110 includes vertical or linear actuators. First, a vertical force is applied to sensor pair 150 while sheet 116 contacts both sensor pairs 150 and 152. Then, while the force is still being applied, the differential displacement of sensor arms 112 of sensor pair 152 is measured. The differential displacement so sensed is indicative of the stiffness of sheet 116.

E. A Fourth Paper Property Sensor System for Measuring Thermal Diffusivity

Figure 5:
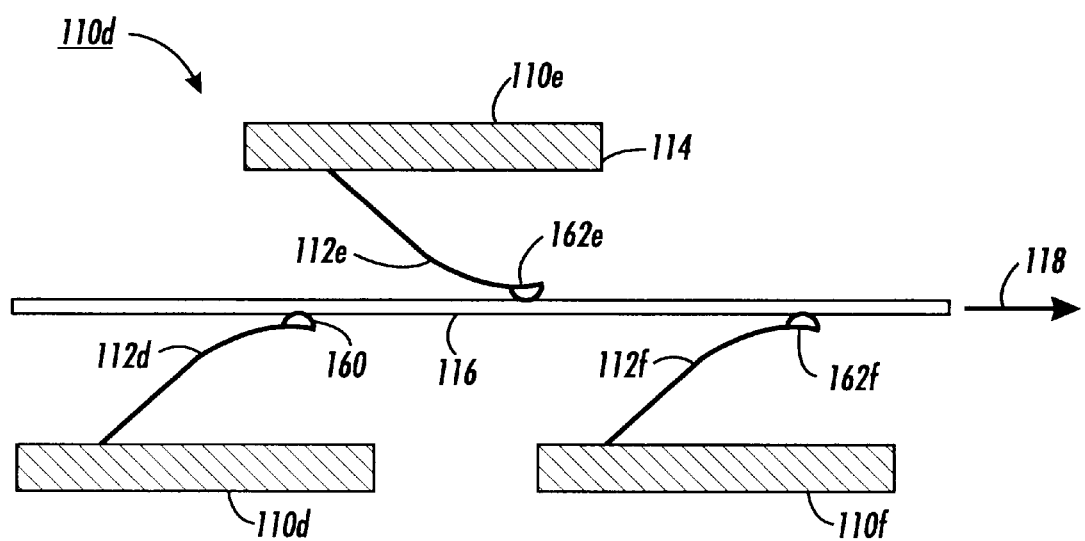
FIG. 5 illustrates an embodiment of a paper property sensor system for measuring paper thermal diffusivity and coefficient of friction.

FIG. 5 illustrates a fourth embodiment 100d of paper property sensor system 100, which can be used to measure the thermal diffusivity directly and to indirectly measure the coefficient of friction of sheet 116. Paper property sensor system 100d includes three paper property sensors 110d, 110e, and 110f. Paper property sensors 110d and 110e are opposed to each other vertically, with paper property sensor 110f spaced apart horizontally from paper property sensor 110d. Paper property sensor 110d includes heater 160, which is attached to the end of sensor arm 112d that contacts paper 116. Heater 160 is a resistive heater deposited on, or incorporated into, sensor arm 112d. A sinusoidal or impulse current drives heater 160. Paper property sensors 110e and 110f each include a temperature sensitive device 162e and 162g located on their sensor arms 112 so that devices 162e and 162f contact sheet 116. Temperature sensitive devices 162e and 162f may be realized as thin film thermocouples or as a temperature sensitive resistors. Vertical or linear actuators can be added to paper property sensors 110d, 110e, and 110f to ensure contact between sensor arms 112d, 112e, and 112f and sheet 116. A thin film coating, such as Si3N4 or diamond, may be deposited on sensor arms 112d, 112e, and 112f to protect them from abrasion by sheet 116.

To sense either vertical or lateral thermal diffusivity, while sheet 116 is stationary a sinusoidal or impulsive current is applied to heater 160. While sheet 116 remains stationary, paper property sensor 110e then senses the heat applied by heater 160, and outputs a signal from thermocouple 162e indicative of the vertical thermal diffusivity of paper 116. Similarly, while sheet 116 remains stationary, paper property sensor 110f senses heat via thermocouple 162f, which outputs a signal indicative of the lateral thermal diffusivity of sheet 116.

Figure 6A:
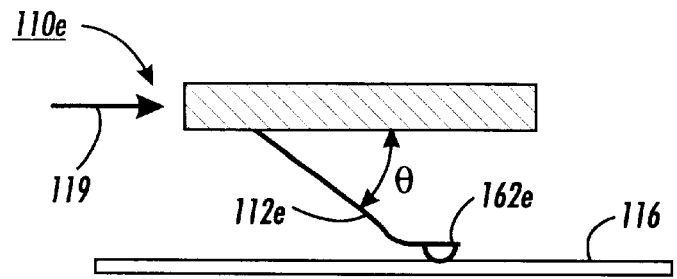
FIG. 6A illustrates an embodiment of a paper property sensor system that measures directly the coefficient of friction of a sheet.

F. A Fifth Paper Property Sensor System for Measuring the Coefficient of Friction FIG. 6A illustrates a fifth embodiment 100e of paper property sensor system 100, which can be used to measure the coefficient of friction of sheet 116. Paper property sensor system 100e includes paper property sensor 110g, which includes temperature sensitive device 162g. Device 162g can be realized using a thermocouple or temperature sensitive resistor. Using system 100e the coefficient of friction can be measured indirectly using at least three different methods.

The first method involves moving sheet 116 past paper property sensor 110g and sensing the temperature of sheet 116 via temperature sensitive device 162g. The resulting temperature increase is proportional to the coefficient of friction, as well as paper velocity, pressure, ambient temperature and paper temperature. As a consequence, to accurately measure the coefficient of friction using this method, reproductive machine 9 must be calibrated for these factors or these factors must be held constant. The second method of indirectly measuring the coefficient of friction involves first holding sheet 116 still for a brief period to calibrate temperature sensitive device 162g. After calibration, sheet 116 is moved past temperature sensitive device 162g, allowing it to sense the temperature of sheet 116. The difference between the temperature sensed while sheet 116 is moving and held stationary is representative of the coefficient of friction of sheet 116. To use the third method, a linear or vertical actuator is added to paper property sensor 110g. Sheet 116 moves past paper property sensor 110g at a constant rate while sensor arm 112 is moved laterally along sheet 116 by the actuator. Measuring θ during this operation yields an indication of the coefficient of friction.

System 100e can be modified to allow direct measurement of the coefficient of friction by omitting temperature sensitive device 162. To make the desired measurement sheet 116 is held stationary and paper property sensor 110g is pushed across sheet 116 while measuring the displacement, θ, which is indicative of the coefficient of friction.

Figure 6B:
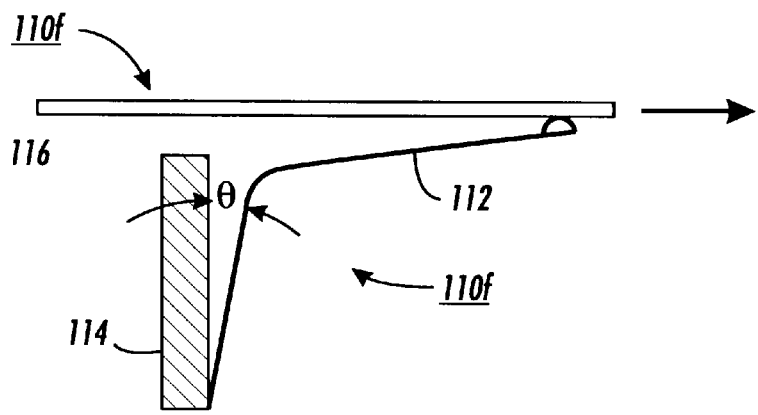
FIG. 6B illustrates another embodiment for indirectly measuring the coefficient of friction of a sheet.

FIG. 6B illustrates an embodiment of paper property sensor system 100f that can also be used to indirectly measure the coefficient of friction. System 100f includes a single paper property sensor 110h, without a thermocouple. Note that unlike other paper property sensors previously discussed, the longitudinal axis of base 114 is perpendicular to the surface of sheet 116. To measure the coefficient of friction with system 100f, paper property sensor 110h is fixed while the lateral motion of sheet 116 is modulated. Deflection of sensor arm 112 then arises from frictional coupling of sheet 116 and the drag of arm 112.

Figure 7:
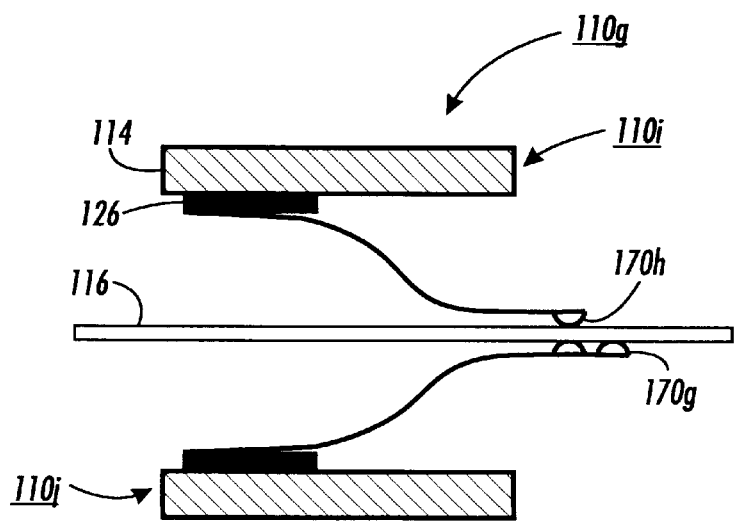
FIG. 7 illustrates an embodiment of a paper property sensor system that measures the dielectric constant of a sheet.

G. A Sixth Paper Property Sensor System for Measuring Dielectric Constant and Resistance FIG. 7 illustrates a sixth embodiment 100g of paper property sensor system 100, which can be used to measure the dielectric constant and resistance of sheet 116. Paper property sensor system 110g includes a pair of opposed paper property sensors 110i and 110j. Both paper property sensors 110i and 110j include vertical actuators 126 to ensure contact with sheet 116. Vertical actuators 126 may be omitted if desired. Each paper property sensor 110i and 110j also includes an electrode 170g and 170h at the end of its associated sensor arm 112. Both electrodes 170g and 170h contact sheet 116.

To measure the dielectric constant, a sinusoidal or impulse voltage is applied to electrode 170g, which is driven through sheet 116 to electrode 170h. The out-of-phase current sensed by electrode 170h is proportional to the capacitance between electrodes 170g and 170h. From the capacitance, C, the dielectric constant, ε, can be calculated using the equation:

$C = \epsilon A / d$ where:

A is the electrode area; and
d is the thickness of the sheet.

The thickness, d, of sheet 116 can be measured using the method discussed with respect to paper property system 100a, illustrated in FIG. 2A.

The resistance of sheet 116 can be measured also by applying an impulse or sinusoidal voltage to electrode 170g and sensing the in-phase current using electrode 170h. This current, indicative of the resistance, strongly depends upon the moisture content of sheet 116 and secondarily on its temperature. Accordingly, reproductive machine 9 should hold these quantities constant or calibrate for them. Alternatively, controller 38 could use changes in the current sensed by electrode 170h to infer changes in the moisture content and temperature of sheet 116.

H. Conclusion

Thus, several paper property sensors have been described that measure a number of interesting paper properties, thereby enabling optimum control of paper paths and process parameters, like fuser temperature. Using relatively simple paper property sensors including a member, base and measurement circuit, the thickness, stiffness, curl, and coefficient of friction of a sheet of material can be measured. Adding vertical actuators to the paper property sensors, permits measurement of sheet mass. Using paper property sensors with heaters and thermocouples permits measurement of thermal diffusivity of sheet, while adding electrodes to a pair of paper property sensors permits measurement of the dielectric constant and resistivity.

In the foregoing specification, the invention has been described with reference to specific exemplary embodiments thereof. It will, however, be evident that various modifications and changes may be made thereto without departing from the broader spirit and scope of the invention as set forth in the appended claims. Accordingly, the specification and drawings are to be regarded in an illustrative rather than a restrictive sense.

What is claimed is:

1. A sensor system for measuring physical properties of a sheet, the sensor system comprising:
   a) a first member and a second member positioned in opposition to each other to each respectively contact the sheet passing therebetween;
   b) a first base coupled to the first member, the first member extending from the first base at a predefined first angle;
   c) a second base coupled to the second member;
   d) a first measurement unit coupled to the first member for measuring the displacement of the first member by measuring a differential change in the predefined first angle as the sheet passes between the first and second members, the first measurement unit including a light source and a light position detector, with light from the light source being reflected from the first member to the light position detector; and
   e) a second measurement unit coupled to the second member for measuring displacement of the second member by measuring a differential change in the predefined angle as the sheet passes between first and second members of the second measurement unit, the second measurement unit including a light source and a light position detector, with light from the light source being reflected from the second member to the light position detector as the sheet passes between the first and second members.

2. A sensor system for measuring physical properties of a sheet, the sensor system comprising:
   a) a first member and a second member positioned in opposition to each other to each respectively contact the sheet passing therebetween;
   b) a first base coupled to the first member, the first member extending from the first base at a predefined first angle;
   c) a second base coupled to the second member;
   d) a first measurement unit coupled to the first member for measuring the displacement of the first member by measuring a differential change in the predefined first angle as the sheet passes between the first and second members, the first measurement unit including a strain gauge coupled to the first member to measure a flexure of the first member; and
   e) a second measurement unit coupled to the second member for measuring displacement of the second member as the sheet passes between the first and second members, the second measurement unit measuring the displacement of the first member by measuring a differential change in the predefined angle as the sheet passes between the first and second members, the first measurement unit including a strain gauge coupled to the second member to measure a flexure of the second member.

3. The sensor system of claim 1, wherein the first and second members comprise a spring.

4. The sensor system of claim 1, wherein the first and second members comprise a linear actuator.

5. The sensor system of claim 1, wherein the first and second members comprise an arm.

6. A sheet handling machine comprising:
   a) a sheet transport mechanism for moving a sheet in response to a control signal;
   b) a controller coupled to the sheet transport mechanism for generating the control signal in response to a first property signal; and
   c) a sensor system coupled to the sheet transport mechanism and generating the first property signal, the sensor system including:
      1) a first member and a second member positioned in opposition to each other to each respectively contact the sheet passing therebetween;
      2) a first base coupled to the first member;
      3) a second base coupled to the second member;
      4) a first measurement unit coupled to the first base for measuring displacement of the first member relative to the first base as the sheet passes between the first and second members; and
      5) a second measurement unit coupled to the second base for measuring displacement of the second member relative to the second base as the sheet passes between the first and second members.

7. The sheet handling machine of claim 6, wherein the first and second members extend from the first base at predefined angles.

8. The sheet handling machine of claim 7, wherein the first and second units measure a differential change in the predefined angles as the sheet passes between the first and second members.

9. The sheet handling machine of claim 8, wherein the first and second measurement units comprise a light source and a light position detector, with light from the light source being reflected from the first and second members to light position detectors.

10. The sheet handling machine of claim 8, wherein the first and second measurement units comprise a strain gauge coupled to the first and second members to measure a flexure of the first and second members.

11. The sheet handling machine of claim 6, wherein the first and second members comprise a spring.

12. The sheet handling machine of claim 6, wherein the first and second members comprise a linear actuator.

* * * * *